United States Patent [19]

DeVilbiss et al.

[11] Patent Number: 5,711,155
[45] Date of Patent: Jan. 27, 1998

[54] TEMPERATURE CONTROL SYSTEM WITH THERMAL CAPACITOR

[75] Inventors: Roger S. DeVilbiss, Dallas; Tony M. Quisenberry, Highland Village; Sathya Rajasubramanian, Arlington; Thomas C. Dedmon, Lewisville, all of Tex.

[73] Assignee: Thermotek, Inc., Carrollton, Tex.

[21] Appl. No.: 574,949

[22] Filed: Dec. 19, 1995

[51] Int. Cl.$^6$ .................................................. F25B 21/02
[52] U.S. Cl. ............................. 62/3.7; 62/3.3; 62/434
[58] Field of Search ............................. 62/3.2, 3.3, 3.7, 62/430, 434, 238.1

[56] References Cited

U.S. PATENT DOCUMENTS

| | | | |
|---|---|---|---|
| 3,481,393 | 12/1969 | Chu | 62/3.7 |
| 3,894,213 | 7/1975 | Agarwala | 219/297 |
| 3,967,627 | 7/1976 | Brown | 128/400 |
| 4,459,468 | 7/1984 | Bailey | 219/490 |
| 4,833,888 | 5/1989 | Kerner et al. | 62/3.3 |
| 4,844,072 | 7/1989 | French et al. | 128/400 |
| 4,962,761 | 10/1990 | Golden | 128/400 |
| 5,097,829 | 3/1992 | Quisenberry | 128/400 |
| 5,128,517 | 7/1992 | Bailey et al. | 219/506 |
| 5,154,661 | 10/1992 | Higgins | 62/3.2 |
| 5,197,294 | 3/1993 | Galvan et al. | 62/3.62 |
| 5,371,665 | 12/1994 | Quisenberry et al. | 363/89 |

Primary Examiner—John M. Sollecito
Attorney, Agent, or Firm—Jenkens & Gilchrist, P.C.

[57] ABSTRACT

An improved thermoelectric temperature control system for selectively heating or cooling a temperature control fluid to be provided through an exit conduit to an external thermal load and returned to the system through an inlet conduit. The system having at least a first liquid heat exchanger, a thermoelectric module in thermal conductivity with the liquid heat exchanger, a heat sink in thermal conductivity with the thermoelectric module, a pump and connecting conduits to move the temperature control fluid from the inlet conduit through the pump and liquid heat exchanger to the exit conduit and power and control electronics to activate the pump and thermoelectric module. The improvement comprises a thermal capacitor connected for fluid communication with the external thermal load and the thermoelectric temperature control system to provide thermal wattage to the external thermal load via the temperature control fluid in addition to the thermal wattage provided to the external thermal load by the thermoelectric temperature control system during the real-time use of the thermoelectric temperature control system. An alternate embodiment includes a liquid-to-liquid heat exchanger system to improve the efficiency of the system.

39 Claims, 8 Drawing Sheets

TEMPERATURE CONTROL SYSTEM WITH THERMAL CAPACITOR

BACKGROUND OF THE INVENTION

1. Field of the Invention

The present invention relates to thermoelectric heating or cooling devices, and more particularly, to the use of a thermal capacitor or storage medium in conjunction with a thermoelectric temperature control system to provide additional heating or cooling capabilities not available by active heating or cooling of the thermoelectric temperature control system.

2. History of the Prior Art

The development of solid state temperature control systems has revolutionized the temperature control industry by providing precise temperature control in a variety of applications where environmental concern, size, weight, performance and noise are at issue.

The most typical thermoelectric device incorporates a thermoelectric module/component that utilizes electrical current to absorb heat from one side of the module and dissipate heat on the opposite side. If the current direction is reversed, so is the heat pumping. Generally, cold sides and hot sides are developed necessitating an effective means of removing or adding heat from or to a solid, liquid or a gas (typically air).

An example of such an application of a thermoelectric device is seen in U.S. Pat. No. 5,097,829 for a temperature controlled cooling system. U.S. Pat. No. 5,371,665 discloses an improved temperature control for thermoelectric modules and also includes bipolar control. The previously mentioned designs rely primarily on the active cooling or heating capacity of these thermoelectric modules/components. Especially at lower temperatures, the efficiency of the thermoelectric modules/components decreases. There is a need to provide additional thermal capacity to enhance the performance of an operating thermoelectric temperature control system in applications where lower temperatures must be reached and significant amounts of cooling are required. One option which is available to provide the additional thermal capacity is to increase the number of thermoelectric modules in the system which increases the initial cost of the system. In addition, it is not considered practical to add thermoelectric modules to a system which is already configured and is being used. An additional option to enhance the performance of the thermoelectric temperature control system is to improve the efficiency of the system. Improved efficiency reduces the work done by the thermoelectric module and hence for a given thermoelectric module, more watts can be pumped. Currently, systems pump the heat to air. The heat from the medium to be cooled is pumped by the thermoelectric module to a heat transfer surface across which ambient air is blown. The air then removes the heat from the heat transfer surface. This is inefficient for several reasons, such as, a) the heat transfer of air is limited, b) Conduction through the heat transfer surface may limit the heat pumping, c) limits on the size of the fan used for blowing the air, etc.

The present invention provides an improvement over the prior art by providing a thermal capacitor in the form of a storage tank containing materials of significant thermal capacity that can be charged with thermal energy prior to the intended, active or real-time use of the thermoelectric temperature control system and provides an economical method of expanding the heating and cooling capacity of the system.

The thermal capacitor, after being charged, can be used to discharge the requisite watts of energy during the use of the thermoelectric temperature control system. While prior systems have a reservoir, the primary purpose of the reservoir is to provide a means to prime, access and recirculate the fluid and not to provide a significant thermal reservoir. All prior systems rely on the active cooling or heating during the intended, active or real-time use and the concept of charge time is negligible. In applications where the charge time is to be significantly reduced, the present invention provides an external port in the reservoir which may be used to add materials (e.g., ice, etc.) which have already been phase changed by other means.

The present invention provides improved efficiency by reducing the temperature drop across the thermoelectric modules by using a liquid having a larger thermal capacity as the medium to which heat is pumped. A radiator is used to remove the heat from the liquid and the liquid can be repeatedly recirculated to improve the efficiency of the system.

SUMMARY OF THE INVENTION

One aspect of the present invention comprises a thermal capacitor connected for fluid communication with an external thermal load and a thermoelectric temperature control system to provide thermal wattage to the external thermal load in addition to the thermal wattage provided to the external thermal load by the thermoelectric temperature control system during the intended or real-time use of the thermoelectric temperature control system.

Another aspect of the present invention comprises a thermal storage tank for storing temperature control fluid for fluid communication with an external thermal load and a thermoelectric temperature control system. Valve means is connected in fluid communication to the thermal storage tank, the external thermal load and the thermoelectric temperature control system to allow thermal wattage to be stored in the temperature control fluid in the thermal storage tank during a charge time prior to the intended use of the thermoelectric temperature control system and to release the stored thermal wattage to the external thermal load during the intended use time of the thermoelectric temperature control system to provide extra wattage capability in addition to the wattage capability of the thermoelectric temperature control system.

Another aspect of the present invention comprises an enlarged reservoir with an external port to facilitate the addition of phase change materials. This embodiment allows for the addition of materials (e.g., ice, etc.) phase changed by external means to reduce the charge time of the thermoelectric temperature control system.

Another aspect of the present invention comprises a liquid heat exchanger having a housing with a conduit therein for passing temperature control fluid therethrough from a thermoelectric temperature control system. Thermal storage material fills the space between the housing and the conduit and is in thermal communication with the conduit. Alternatively, the thermal storage material could be stored in a container within the housing and the cooling or warming fluid could flow external to the container and internal to the housing. Valve means is connected in fluid communication to the liquid heat exchanger, the external thermal load and the thermoelectric temperature control system to allow thermal wattage to be stored in the thermal storage material in the housing during a charge time prior to the intended use of the thermoelectric temperature control system and to release the stored thermal wattage to the temperature control fluid and then to the external thermal load during the intended use time of the thermoelectric temperature control system to provide extra wattage capability in addition to the wattage capability of the thermoelectric temperature control system.

Another aspect of the present invention provides improved efficiency by reducing the temperature drop across the thermoelectric modules by using a liquid having a larger thermal capacity as the medium to which heat is pumped. A radiator is used to remove the heat from the liquid and the liquid can be repeatedly recirculated to improve the efficiency of the system. This liquid is circulated in a counter-flow manner with respect to the temperature control fluid to improve the efficiency of the system.

Another aspect of the present invention provides improved efficiency by reducing the temperature drop across the thermoelectric modules by using a liquid having a larger thermal capacity as the medium to which heat is pumped. A continuous external source of water is used to remove the heat from the heat transfer surface and the water is then disposed of through a drain system. This liquid is circulated in a counter-flow manner with respect to the temperature control fluid to improve the efficiency of the system. A pressure regulator may be used at the inlet to the liquid heat exchanger to regulate the inlet pressure from the continuous external source of water. A flow control valve may be used at the outlet of the liquid heat exchanger to control the flow rate of the water. The flow control valve may be temperature regulated to vary the flow depending upon the hot side temperatures.

Another aspect of the present invention provides a quick changeover capability from the cooling mode to the heating mode or vice versa. Separate reservoirs are provided for the heating mode and the cooling mode. Valve means provides for switching between the separate reservoirs and applying the desired reservoir to the external thermal load for the desired mode of operation.

BRIEF DESCRIPTION OF THE DRAWINGS

Other advantages and features of the invention will become more apparent with reference to the following detailed description of a presently preferred embodiment thereof in connection with the accompanying drawings, wherein like reference numerals have been applied to like elements, in which.

DETAILED DESCRIPTION

Figure 1:
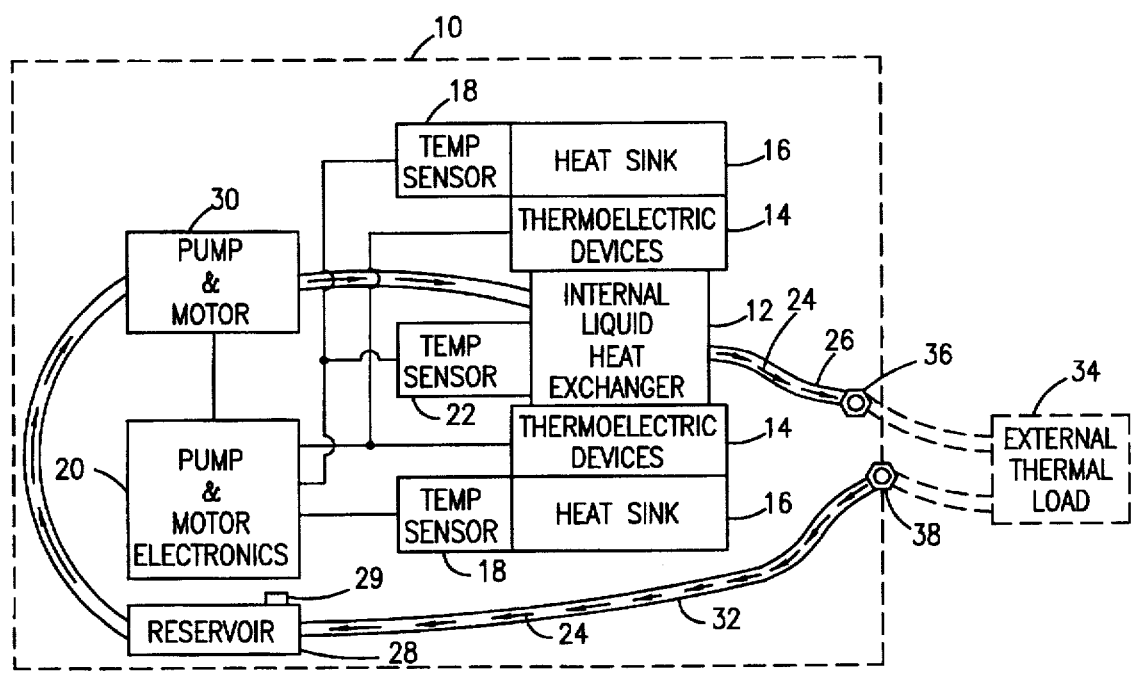
FIG. 1 is a block diagram showing the relationship of the components in a typical prior art thermoelectric temperature control system.

Referring to FIG. 1, there is shown in block diagram form, an exemplary prior art thermoelectric temperature control system 10 constructed in accordance with the teachings of U.S. Pat. Nos. 5,097,829 and 5,371,665, incorporated herein by reference. Thermoelectric temperature control system 10, for either heating or cooling, includes an internal liquid heat exchanger 12, at least one thermoelectric device or module 14 attached to internal liquid heat exchanger 12 for thermal conductivity therebetween, a heat sink 16 attached to thermoelectric device or module 14 for thermal conductivity therebetween, a temperature sensor 18 attached to heat sink 16 to provide a signal to the power and control electronics circuitry 20 indicative of the temperature of heat sink 16. A temperature sensor 22 is attached to internal liquid heat exchanger 12 to provide a signal to the power and control electronics circuitry 20 indicative of the temperature of internal liquid heat exchanger 12. Power and control circuitry 20 provides power, of the correct polarity and duration, to the thermoelectric device or module 14 so that the desired cooling or heating of the temperature control fluid 24 (such as water, glycol solution, etc.) in the exit hose or tubing 26 from the internal liquid heat exchanger 12 will be accomplished. Fluid containing reservoir 28 is connected in fluid communicating relation with pump and motor 30 and inlet hose or pipe 32. The external thermal load or liquid circulation manifold or heat exchanger 34 is connected to inlet hose 32 and exit hose 26 of the thermoelectric temperature control system 10 via connectors 36 and 38. The prior art thermoelectric temperature control systems rely on the active cooling or heating capacity of the thermoelectric device or module during the intended or real-time use of the systems. If the required heating or cooling capacity of the thermoelectric temperature control system 10 is not sufficient for the particular job or use, then additional thermoelectric devices or modules must be incorporated into the system or a different system must be provided.

The present invention provides a solution for a thermoelectric temperature control system which does not have enough thermal capacity for the desired function by providing means for incorporating additional thermal wattage to the existing system without making physical changes to the thermoelectric temperature control system. In addition, the present invention can be incorporated into a thermoelectric temperature control system during the manufacture of the system. In applications where the charge time is to be significantly reduced, the present invention provides an external port 29 in reservoir 28 (see FIG. 1) which may be used to add materials (e.g., ice, etc.) which have already been phase changed by other means.

Figure 2:
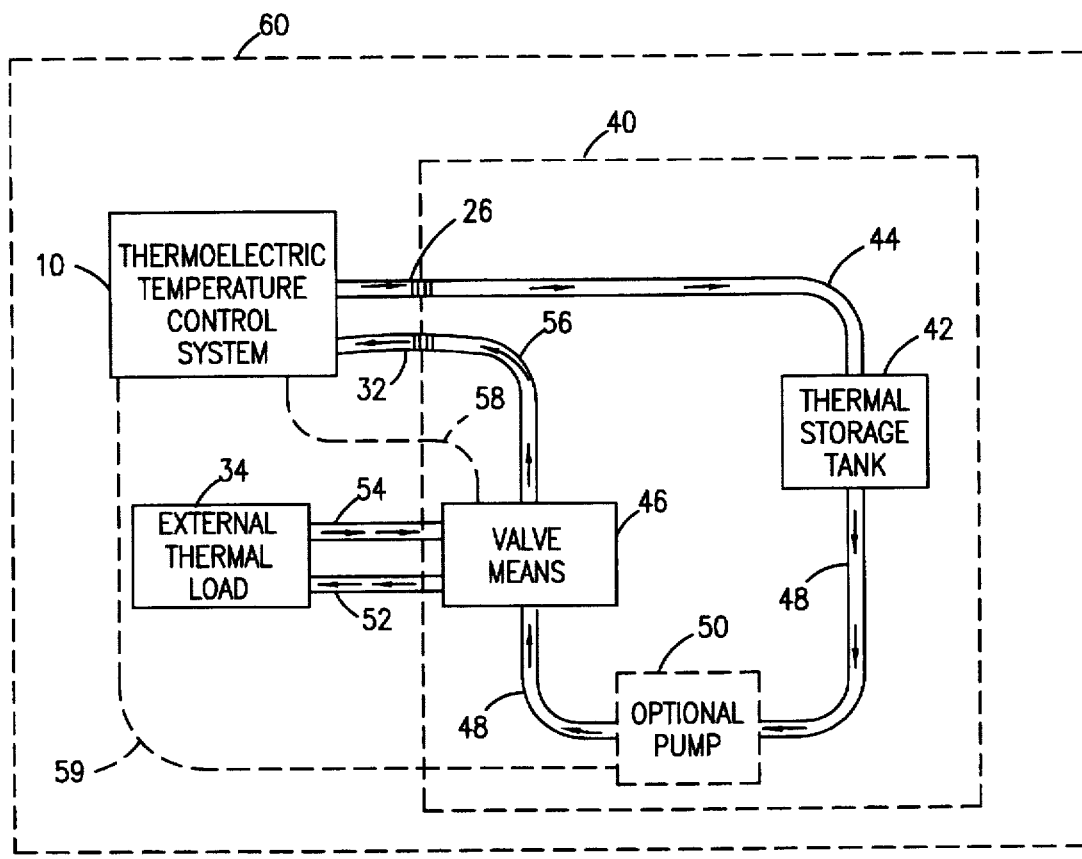
FIG. 2 is a schematic view showing one embodiment of the present invention as connected to an exemplary prior art thermoelectric temperature control system.

Referring now to FIG. 2, the reference numeral 40 generally indicates one embodiment of the present invention as add-on apparatus to a thermoelectric temperature control system for providing additional thermal wattage during the time of intended use of the thermoelectric temperature control system 10 for use in either heating or cooling. Thermal capacitor 40 includes a thermal storage tank 42 connected in fluid communication with exit hose or tubing 26 of thermoelectric temperature control system 10 by hose or tubing 44. Thermal storage tank 42 is connected to valve means 46 by hose or tubing 48. If the present heating or cooling function requires additional thermal pumping capacity, optional pump 50 may be installed in hose or tubing 48 between thermal storage tank 42 and valve means 46. Valve means 46 is operationally connected to the external thermal load 34 by hoses or tubing 52 and 54. Valve means 46 is also operationally connected to inlet hose or pipe 32 of thermoelectric temperature control system 10 by hose or tubing 56. It will be appreciated that thermal storage tank 42, valve means 46 and optional pump 50 are not limited to their disclosed sequential position in the fluid loop shown in FIG. 2 but their respective sequential positions may be changed without deviating from the concept of the present invention. Valve means 46 and optional pump 50 may also be connected to power and control electronics circuitry 20 (see FIG. 1) by cables 58 and 59, respectively, so the valves and pump may be activated and deactivated at the appropriate times by the power and control electronics circuitry 20, especially when thermal capacitor 40 is incorporated into a thermoelectric temperature system during manufacture to form a stand-alone unit 60. It will be appreciated that during manufacture to form a stand-alone unit 60, reservoir 28 (see FIG. 1) could be eliminated. It will be appreciated that valve means 46 and optional pump 50 of the add-on apparatus may be controlled by separate control circuitry or be connected to power and control electronics circuitry 20 by cables 58 and 59, respectively.

With further reference to FIG. 2, in preparation for use of the thermoelectric temperature control system 10 and thermal capacitor 40, power is applied to thermoelectric temperature control system 10 and valve means 46 is activated to connect hose or tubing 48 to hose or tubing 56 so as to bypass the external thermal load. The thermoelectric temperature control system 10 is run for a period of time called the charge time, prior to the period of intended use, to heat or cool the temperature control fluid 24 which includes the amount of extra temperature control fluid 24 held in the thermal capacitor 40. Upon completion of the charge time, valve means 46 is activated to connect hose or tubing 48 to hose or tubing 52 and to also connect hose or tubing 54 to hose or tubing 56. The temperature control fluid 24 in the thermal capacitor 40 then releases or absorbs heat during the intended use of the thermoelectric temperature control system 10 and thus economically generates the extra wattage requirements needed by the external thermal load 34 in addition to the active heating or cooling provided by the thermoelectric temperature control system 10. Applications such as temperature controlled baths, delivery of temperature controlled cardioplegia solutions, body fluids and other infusates would be typical areas where additional thermal capacity would be needed and used.

Figure 3:
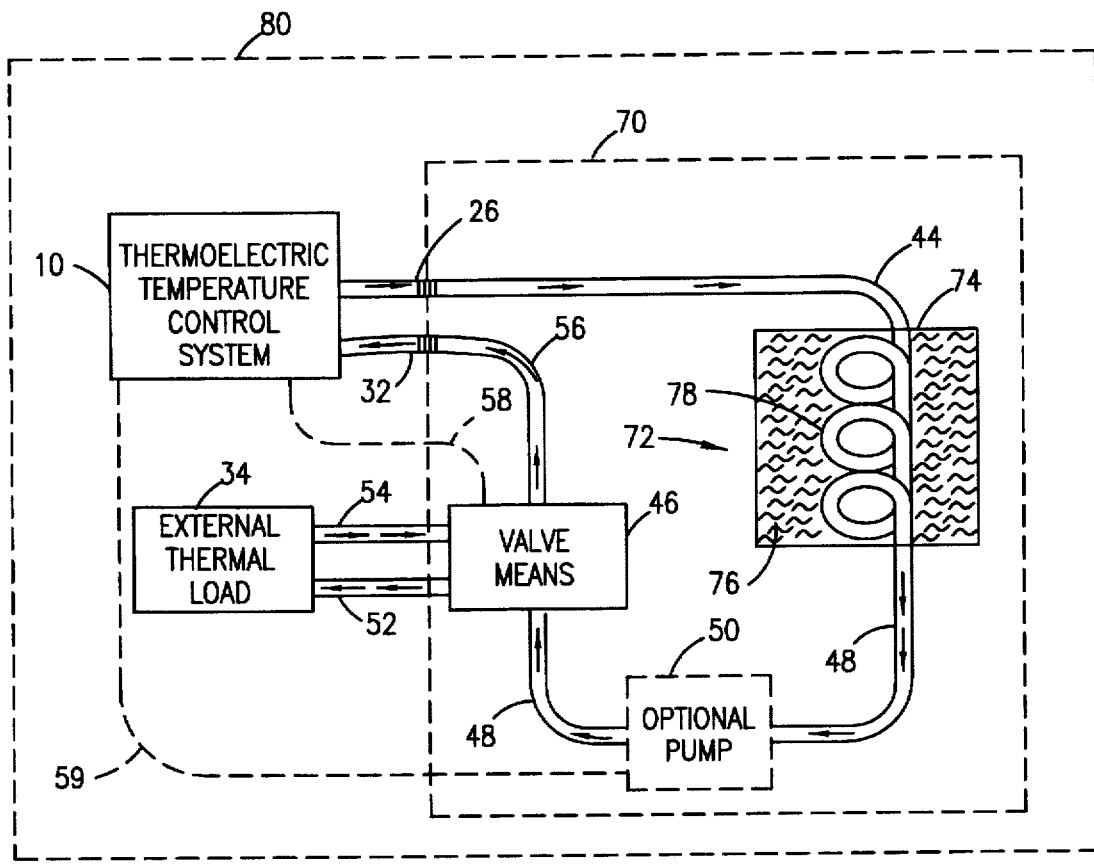
FIG. 3 is a schematic view showing an additional embodiment of the present invention as connected to an exemplary prior art thermoelectric temperature control system.

Referring now to FIG. 3, the reference numeral 70 generally indicates an additional embodiment of the present invention as add-on apparatus to a thermoelectric temperature control system for providing additional thermal wattage during the time of intended use of the thermoelectric temperature control system 10 for either heating or cooling. Thermal capacitor 70 includes an external heat exchanger 72 connected in fluid communication with exit hose or tubing 26 of thermoelectric temperature control system 10 by hose or tubing 44. External heat exchanger 72 comprises a tank or housing 74 containing thermal storage material 76 surrounding tubing 78 and in thermal communication therewith. Thermal storage material 76 comprises a phase change material or a material with a large specific heat factor. Such materials include waxes, paraffins, water, salts, etc. Tubing 78 is operatively connected for fluid communication between hose or tubing 44 and hose or tubing 48. External heat exchanger 72 is connected to valve means 46 by hose or tubing 48. If the present heating or cooling function requires additional thermal pumping capacity, optional pump 50 may be installed in hose or tubing 48 between external heat exchanger 72 and valve means 46. Valve means 46 is operationally connected to the external thermal load 34 by hoses or tubing 52 and 54. Valve means 46 is also operationally connected to inlet hose or pipe 32 of thermoelectric temperature control system 10 by hose or tubing 56. It will be appreciated that external heat exchanger 72, valve means 46 and optional pump 50 are not limited to their disclosed sequential position in the fluid loop shown in FIG. 3 but their respective sequential positions may be changed without deviating from the concept of the present invention. Valve means 46 and optional pump 50 may also be connected to power and control electronics circuitry 20 (see FIG. 1) by cables 58 and 59, respectively, so the valves and pump may be activated and deactivated at the appropriate times by the power and control electronics circuitry 20, especially when thermal capacitor 70 is incorporated into a thermoelectric temperature system during manufacture to form a stand-alone unit 80. It will be appreciated that valve means 46 and optional pump 50 of the add-on apparatus may be controlled by separate control circuitry or be connected to power and control electronics circuitry 20 by cables 58 and 59, respectively.

With further reference to FIG. 3, in preparation for use of the thermoelectric temperature control system 10 and thermal capacitor 70, power is applied to thermoelectric temperature control system 10 and valve means 46 is activated to connect hose or tubing 48 to hose or tubing 56 so as to bypass the external thermal load 34. The thermoelectric temperature control system 10 is run for a period of time called the charge time, prior to the period of intended use, to not only heat or cool the temperature control fluid 24 but to also heat or cool the thermal storage material 76 held in the external heat exchanger 72 of thermal capacitor 70. Upon completion of the charge time, valve means 46 is activated to connect hose or tubing 48 to hose or tubing 52 and to also connect hose or tubing 54 to hose or tubing 56. The thermal storage material 76 held in the external heat exchanger 72 then releases or absorbs heat to or from the temperature control fluid 24 flowing through tubing 78 during the intended use of the thermoelectric temperature control system 10 and thus economically generates the extra wattage requirements needed by the external thermal load 34 in addition to the active heating or cooling provided by the thermoelectric temperature control system 10.

Figure 4:
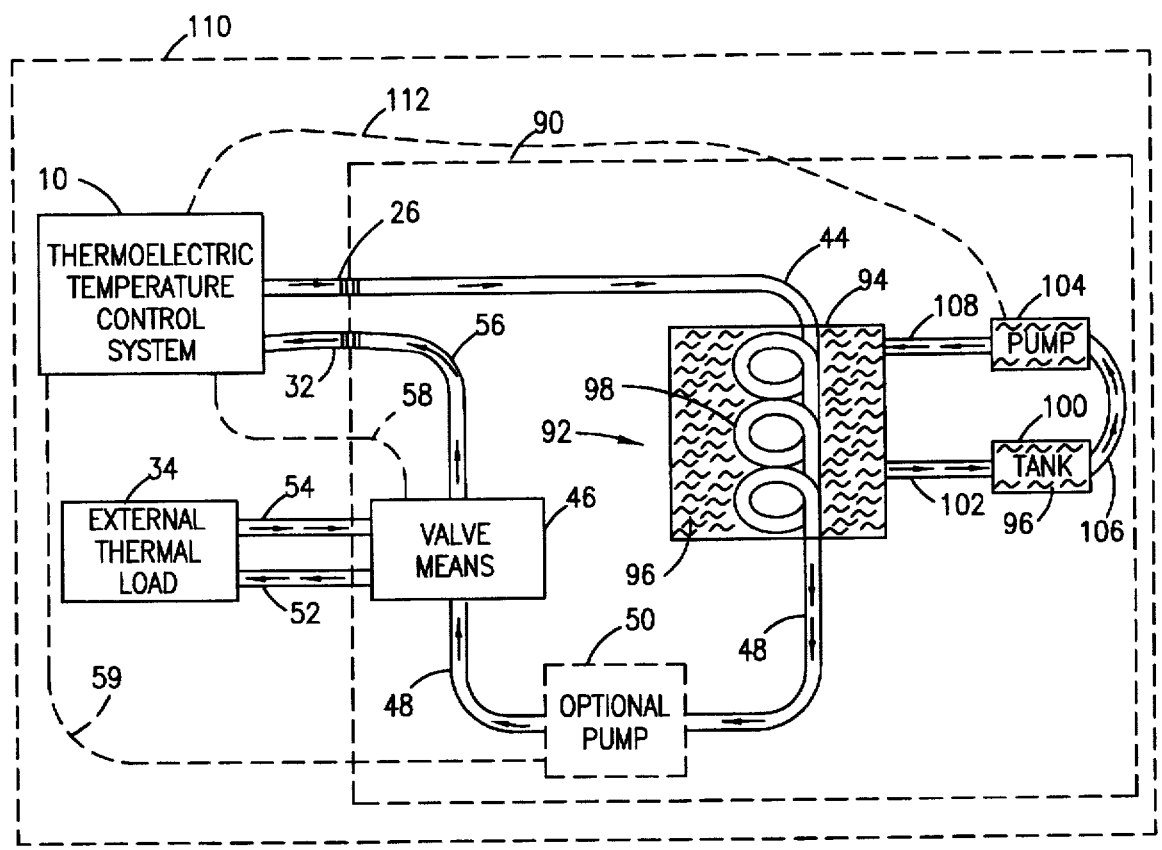
FIG. 4 is a schematic view showing an additional embodiment of the present invention as connected to an exemplary prior art thermoelectric temperature control system.

Referring now to FIG. 4, the reference numeral 90 generally indicates an additional embodiment of the present invention as add-on apparatus to a thermoelectric temperature control system for providing additional thermal wattage during the time of intended use of the thermoelectric temperature control system 10 for either heating or cooling.

Thermal capacitor 90 includes an external heat exchanger 92 connected in fluid communication with exit hose or tubing 26 of thermoelectric temperature control system 10 by hose or tubing 44. External heat exchanger 92 comprises a tank or housing 94 containing thermal storage material 96 surrounding tubing 98 and in thermal communication therewith. Thermal storage material 96 comprises a phase change material or a material with a large specific heat factor. Such materials include waxes, paraffins, water, salts, etc. Tubing 98 is operatively connected for fluid communication between hose or tubing 44 and hose or tubing 48. External heat exchanger 92 is connected to valve means 46 by hose or tubing 48. The thermal storage material 96 is in fluid communication with storage tank 100 by hose or tubing 102. Storage tank 100 is in fluid communication with pump 104 by hose or tubing 106 while pump 104 is in fluid communication with thermal storage material 96 by hose or tubing 108. If the present heating or cooling function requires additional thermal pumping capacity, optional pump 50 may be installed in hose or tubing 48 between external heat exchanger 92 and valve means 46. Valve means 46 is operationally connected to the external thermal load 34 by hoses or tubing 52 and 54. Valve means 46 is also operationally connected to inlet hose or pipe 32 of thermoelectric temperature control system 10 by hose or tubing 56. It will be appreciated that external heat exchanger 92, valve means 46 and optional pump 50 are not limited to their disclosed sequential position in the fluid loop shown in FIG. 4 but their respective sequential positions may be changed without deviating from the concept of the present invention. Valve means 46, optional pump 50 and pump 104 may also be connected to power and control electronics circuitry 20 (see FIG. 1) by cables 58, 59 and 112 respectively, so the valves and pump may be activated and deactivated at the appropriate times by the power and control electronics circuitry 20, especially when thermal capacitor 90 is incorporated into a thermoelectric temperature system during manufacture to form a stand-alone unit 110. It will be appreciated that valve means 46, optional pump 50 and pump 104 of the add-on apparatus may be controlled by separate control circuitry or be connected to power and control electronics circuitry 20 by cables 58, 59 and 112, respectively.

With further reference to FIG. 4, in preparation for use of the thermoelectric temperature control system 10 and thermal capacitor 90, power is applied to thermoelectric temperature control system 10 and valve means 46 is activated to connect hose or tubing 48 to hose or tubing 56 so as to bypass the external thermal load 34. The thermoelectric temperature control system 10 is run for a period of time called the charge time, prior to the period of intended use, to not only heat or cool the temperature control fluid 24 but to also heat or cool the thermal storage material 96 held in the external heat exchanger 92 and in storage tank 100 of thermal capacitor 90. Upon completion of the charge time, valve means 46 is activated to connect hose or tubing 48 to hose or tubing 52 and to also connect hose or tubing 54 to hose or tubing 56. The thermal storage material 96 held in the external heat exchanger 92 and in storage tank 100 is circulated by pump 104 and releases or absorbs heat to or from the temperature control fluid 24 flowing through tubing 98 during the intended use of the thermoelectric temperature control system 10 and thus economically generates the extra wattage requirements needed by the external thermal load 34 in addition to the active heating or cooling provided by the thermoelectric temperature control system 10. Pump 104 and storage tank 100 results in the thermal storage material 96 supplying heat or cold in a faster manner than the embodiment of FIGS. 2 and 3 and provides a higher efficiency of operation.

Figure 5:
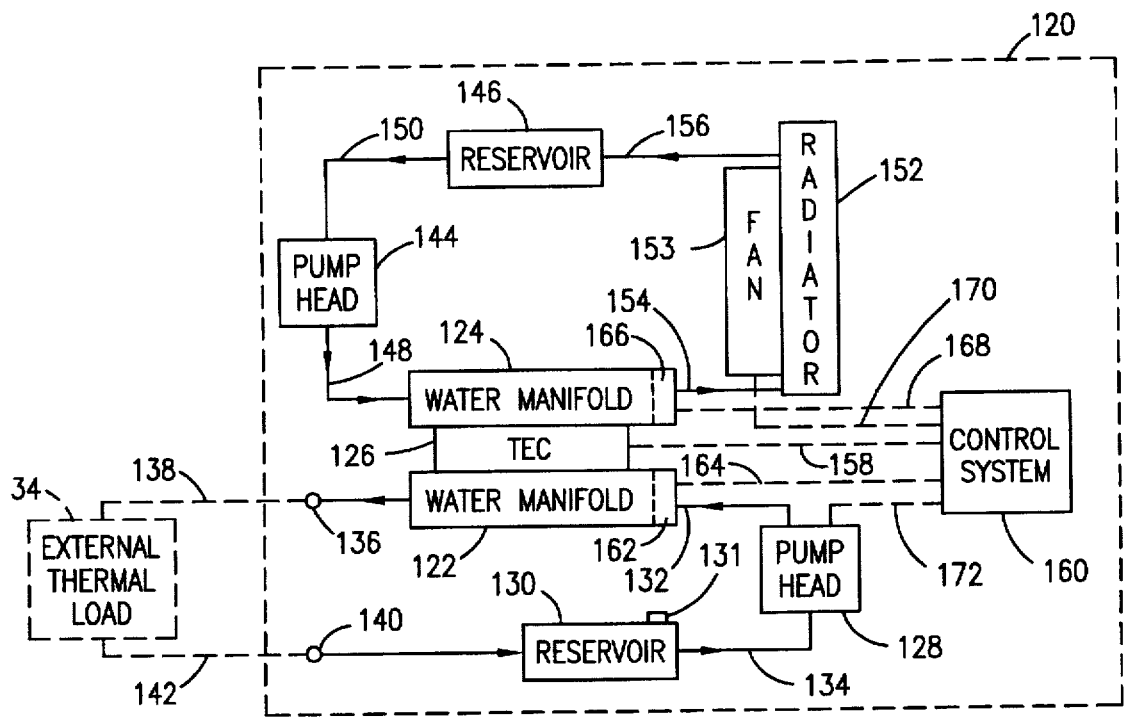
FIG. 5 is a schematic view showing an additional embodiment of the present invention which improves the efficiency of the thermoelectric temperature control system.

Referring now to FIG. 5, the reference numeral 120 indicates an additional embodiment of the present invention which provides a thermoelectric temperature control system with an improved efficiency. Thermoelectric temperature control system 120, for either heating or cooling, includes a first liquid heat exchanger or water manifold 122 and a second liquid heat exchanger or water manifold 124. At least one thermoelectric device or module (TEC) 126 is positioned in contact with the first liquid heat exchanger 122 and the second liquid heat exchanger 124 for thermal conductivity therebetween. First pump head 128 is connected in fluid communication with first liquid heat exchanger 122 and with reservoir 130 by conduits, pipes or hoses 132 and 134, respectively. First liquid heat exchanger 122 is also connected in fluid communication with external load 34 via liquid outlet 136 and conduit, pipe or hose 138. Reservoir 130 is also connected in fluid communication with external load 34 via liquid inlet 140 and conduit, pipe or hose 142. Control system 160 provides power, of the correct polarity and duration, to thermoelectric device or module 126 via cable 158 so that the desired cooling or heating of the temperature control fluid 24 (such as water, glycol solution, etc.) flowing through first liquid heat exchanger 122 will be accomplished. Temperature sensor 162 is attached to first liquid heat exchanger 122 to provide a signal via cable 164 to the control system 160 indicative of the temperature of the first liquid heat exchanger 122. It will be appreciated that temperature control fluid 24 is circulated through first liquid heat exchanger 122, external thermal load 34, reservoir 130, first pump head 128 and back to first liquid heat exchanger 122.

In applications where the charge time is to be significantly reduced, the present invention provides an external port 131 in reservoir 130 which may be used to add materials (e.g., ice, etc.) which have already been phase changed by other means.

Second pump head 144 is connected in fluid communication with second liquid heat exchanger 124 and with reservoir 146 by conduits, pipes or hoses 148 and 150, respectively. It will be appreciated that first pump head 128 and second pump head 144 are combined with a pump motor to comprise a two head pump. Second liquid heat exchanger 124 is also connected in fluid communication with radiator 152 via conduit, pipe or hose 154. Radiator 152 is also connected in fluid communication with reservoir 146 via conduit, pipe or hose 156. Fan 153 is positioned to blow or pass a gaseous fluid, such as air, etc., over radiator 152 to cool the liquid passing through radiator 152. Using radiator 152 to remove the heat or cold from the liquid passing through second liquid heat exchanger 124, the liquid can be repeatedly recirculated to improve the efficiency of the system. Typically, this liquid is circulated counter current to the flow of the temperature control fluid 24 but other embodiments providing co-flow or cross-flow are available embodiments. Temperature sensor 166 is attached to second liquid heat exchanger 124 to provide a signal via cable 168 to the control system 160 indicative of the temperature of the second liquid heat exchanger 124. Fan cable 170. It will be appreciated that a liquid with a larger thermal capacity than air is circulated through second liquid heat exchanger 124, radiator 152, reservoir 146, second pump head 144 and back to second liquid heat exchanger 124.

Control system 160 receives an indication of the temperature of the temperature control fluid 24 from the temperature sensor 162 and of the temperature of the liquid flowing through the second liquid heat exchanger 124 from the temperature sensor 166. Based upon these sensed temperatures, control system 160 sends controlling signals to thermoelectric device or module 126, to pump motor (via cable 172) to control first pump head 128 and second pump head 144 and to fan 153 to maintain the temperature of the temperature control fluid 24 at the desired value for the particular function being performed.

Figure 6:
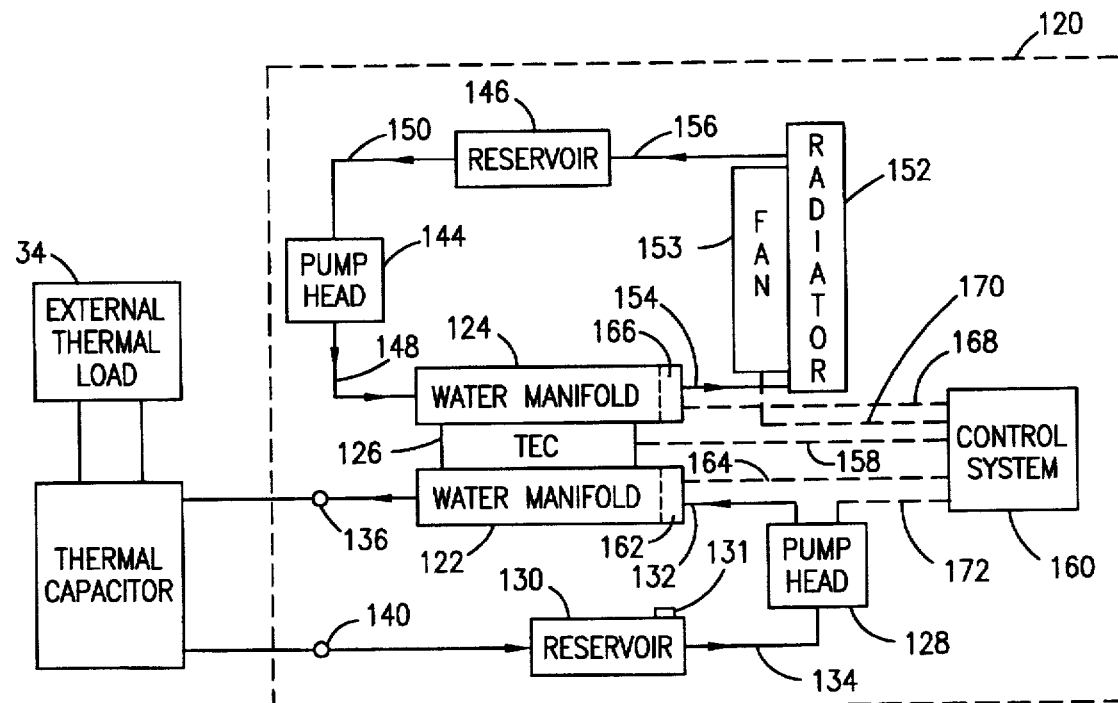
FIG. 6 is a schematic view showing an additional embodiment of the present invention which expands the heating and cooling capacity of the thermoelectric temperature control system.

Referring now to FIG. 6, there is shown in block diagram form, thermoelectric temperature control system 120 with a thermal capacitor 40, 70 or 90 for providing additional thermal wattage during the time of intended use of the thermoelectric temperature control system 120.

Figure 7:
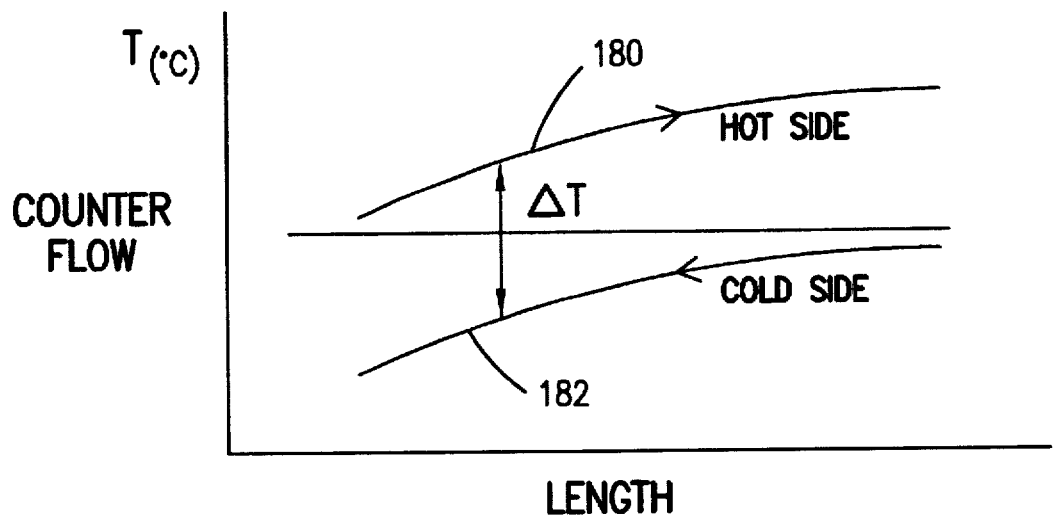
FIG. 7 is a graph illustrating the temperature relationship between the hot and cold side of the thermoelectric temperature control systems of FIGS. 5 and 6 during counter flow of the liquids.

FIG. 7 shows a graph indicating the temperature relationship between the hot side and the cold side of the thermoelectric temperature control system 120 when the temperature control fluid 24 flowing through first liquid heat exchanger 122 is flowing counter to the direction of flow of the liquid flowing through the second liquid heat exchanger 124. This depiction is when the thermoelectric temperature control system 120 is being operated to cool the temperature control fluid 24 (cold side) flowing through the first liquid heat exchanger 122. The bottom curve 182 indicates the temperature of the temperature control fluid 24 as it flows along the length of first liquid heat exchanger 122. The top curve 180 indicates the temperature of the liquid as it flows along the length of second liquid heat exchanger 124. Counter flow of the liquids helps maintain an almost uniform small temperature difference across the thermoelectric device or module 126 thereby improving the efficiency of the system.

Figure 8:
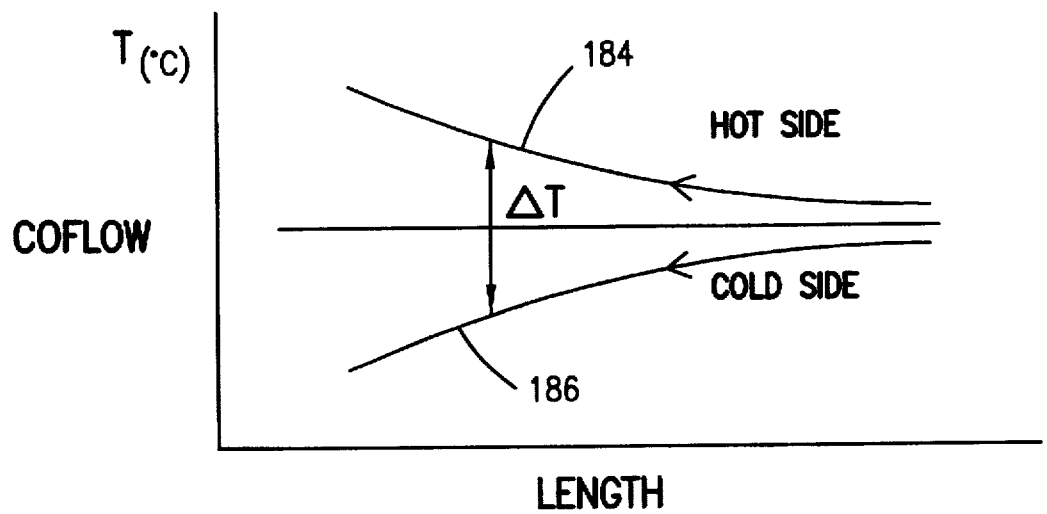
FIG. 8 is a graph illustrating the temperature relationship between the hot and cold side of the thermoelectric temperature control systems of FIGS. 5 and 6 during co-flow of the liquids.

FIG. 8 shows a graph indicating the temperature relationship between the hot side and the cold side of the thermoelectric temperature control system 120 when the temperature control fluid 24 flowing through first liquid heat exchanger 122 is flowing in the same direction (co-flow) as the flow of the liquid flowing through the second liquid heat exchanger 124. This depiction is when the thermoelectric temperature control system 120 is being operated to cool the temperature control fluid 24 (cold side) flowing through the first liquid heat exchanger 122. The bottom curve 186 indicates the temperature of the temperature control fluid 24 as it flows along the length of first liquid heat exchanger 122. The top curve 184 indicates the temperature of the liquid as it flows along the length of second liquid heat exchanger 124.

Figure 9:
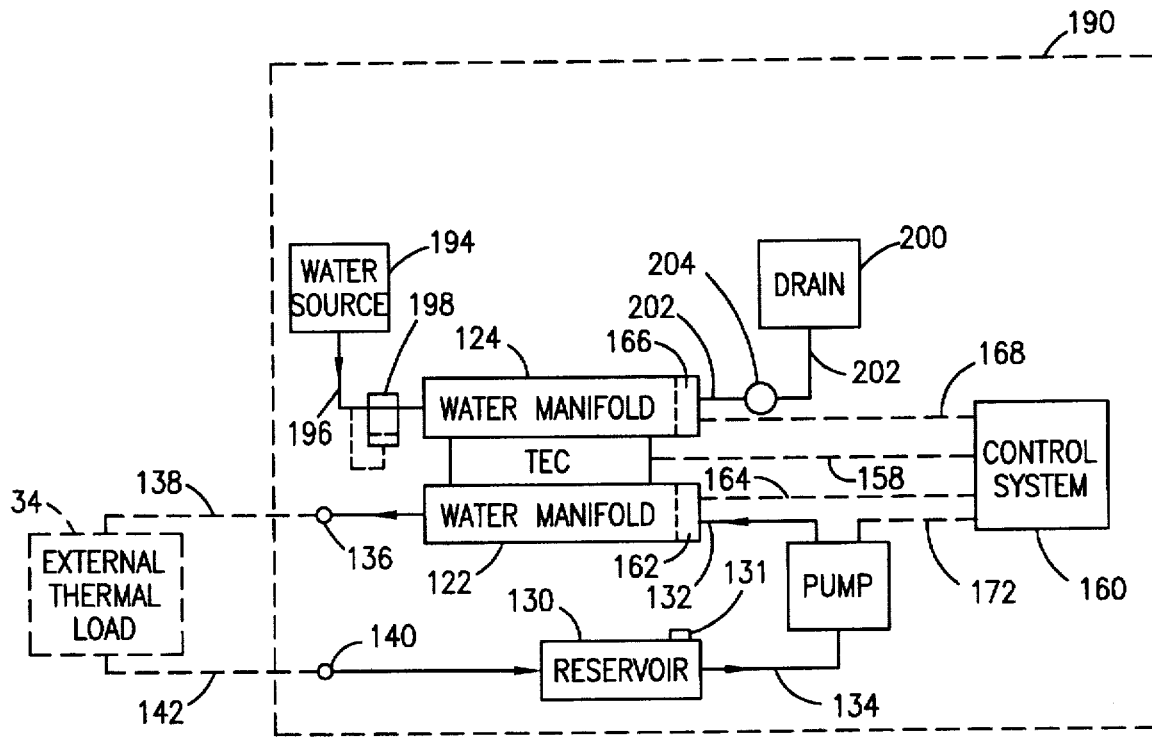
FIG. 9 is a schematic view showing an additional embodiment of the present invention which improves the efficiency of the thermoelectric temperature control system.

Referring now to FIG. 9, the reference numeral 190 indicates an additional embodiment of the present invention which provides a thermoelectric temperature control system with an improved efficiency. Thermoelectric temperature control system 190, for either heating or cooling, includes a first liquid heat exchanger or water manifold 122 and a second liquid heat exchanger or water manifold 124. At least one thermoelectric device or module (TEC) 126 is positioned in contact with the first liquid heat exchanger 122 and the second liquid heat exchanger 124 for thermal conductivity therebetween. Pump 192 is connected in fluid communication with first liquid heat exchanger 122 and with reservoir 130 by conduits, pipes or hoses 132 and 134, respectively. First liquid heat exchanger 122 is also connected in fluid communication with external load 34 via liquid outlet 136 and conduit, pipe or hose 138. Reservoir 130 is also connected in fluid communication with external load 34 via liquid inlet 140 and conduit, pipe or hose 142. Control system 160 provides power, of the correct polarity and duration, to thermoelectric device or module 126 via cable 158 so that the desired cooling or heating of the temperature control fluid 24 (such as water, glycol solution, etc.) flowing through first liquid heat exchanger 122 will be accomplished. Temperature sensor 162 is attached to first liquid heat exchanger 122 to provide a signal via cable 164 to the control system 160 indicative of the temperature of the first liquid heat exchanger 122. It will be appreciated that temperature control fluid 24 is circulated through first liquid heat exchanger 122, external thermal load 34, reservoir 130, pump 192 and back to first liquid heat exchanger 122.

In applications where the charge time is to be significantly reduced, the present invention provides an external port 131 in reservoir 130 which may be used to add materials (e.g., ice, etc.) which have already been phase changed by other means.

A continuous external source of water 194 is connected in fluid communication with second liquid heat exchanger 124 by conduit, pipe or hose 196. Pressure regulator 198 is connected in conduit, pipe or hose 196 between the continuous external source of water 194 and second liquid heat exchanger 124 to regulate the inlet pressure of the water to the second liquid heat exchanger 124. Second liquid heat exchanger 124 is also connected in fluid communication with drain 200 via conduit, pipe or hose 202. Flow control valve 204 is connected in conduit, pipe or hose 202 to control the flow rate of the water through second liquid heat exchanger 124. Flow control valve 204 may be temperature regulated to vary the flow of the water dependent upon the hot side temperature. Typically, the flow of the continuous external source of water is circulated counter current to the flow of the temperature control fluid 24 but other embodiments providing co-flow or cross-flow are available embodiments. Temperature sensor 166 is attached to second liquid heat exchanger 124 to provide a signal via cable 168 to the control system 160 indicative of the temperature of the second liquid heat exchanger 124.

Control system 160 receives an indication of the temperature of the temperature control fluid 24 from the temperature sensor 162 and of the temperature of the liquid flowing through the second liquid heat exchanger 124 from the temperature sensor 166. Based upon these sensed temperatures, control system 160 sends controlling signals to thermoelectric device or module 126, to pump 192 (via cable 172) to maintain the temperature of the temperature control fluid 24 at the desired value for the particular function being performed.

Figure 10:
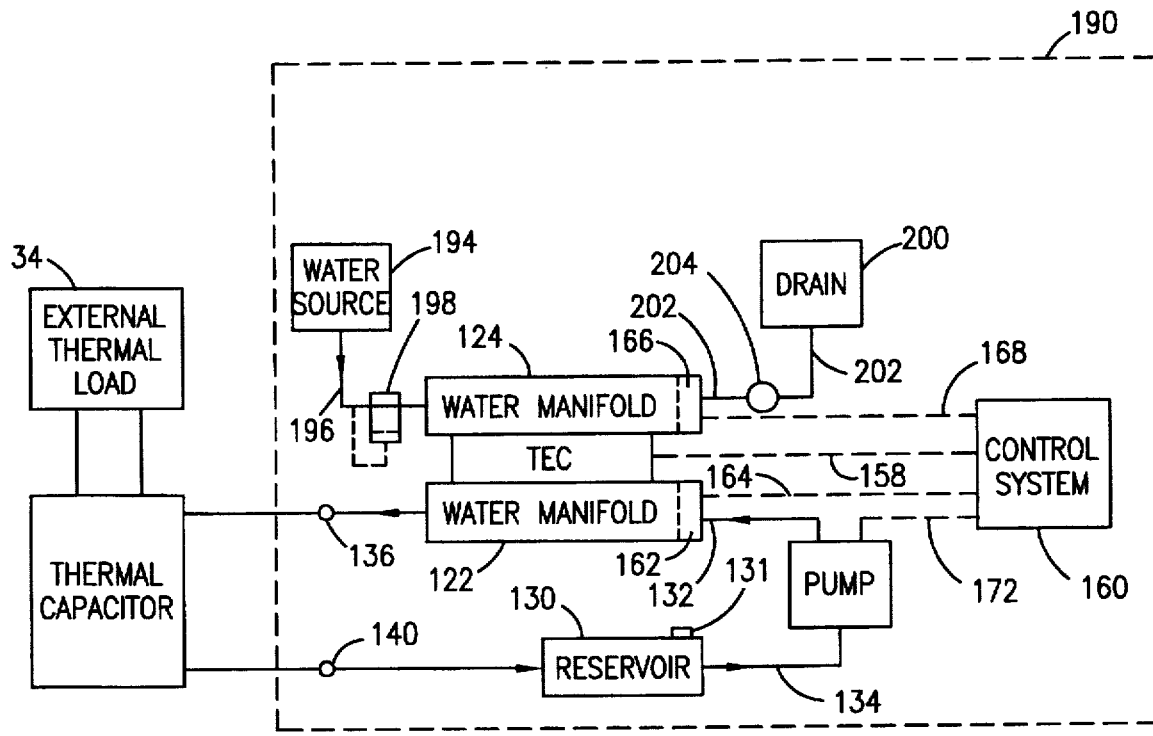
FIG. 10 is a schematic view showing an additional embodiment of the present invention which expands the heating and cooling capacity of the thermoelectric temperature control system.

Referring now to FIG. 10, there is shown in block diagram form, thermoelectric temperature control system 9 with a thermal capacitor 40, 70 or 90 for providing additional thermal wattage during the time of intended use of the thermoelectric temperature control system 9.

Figure 11:
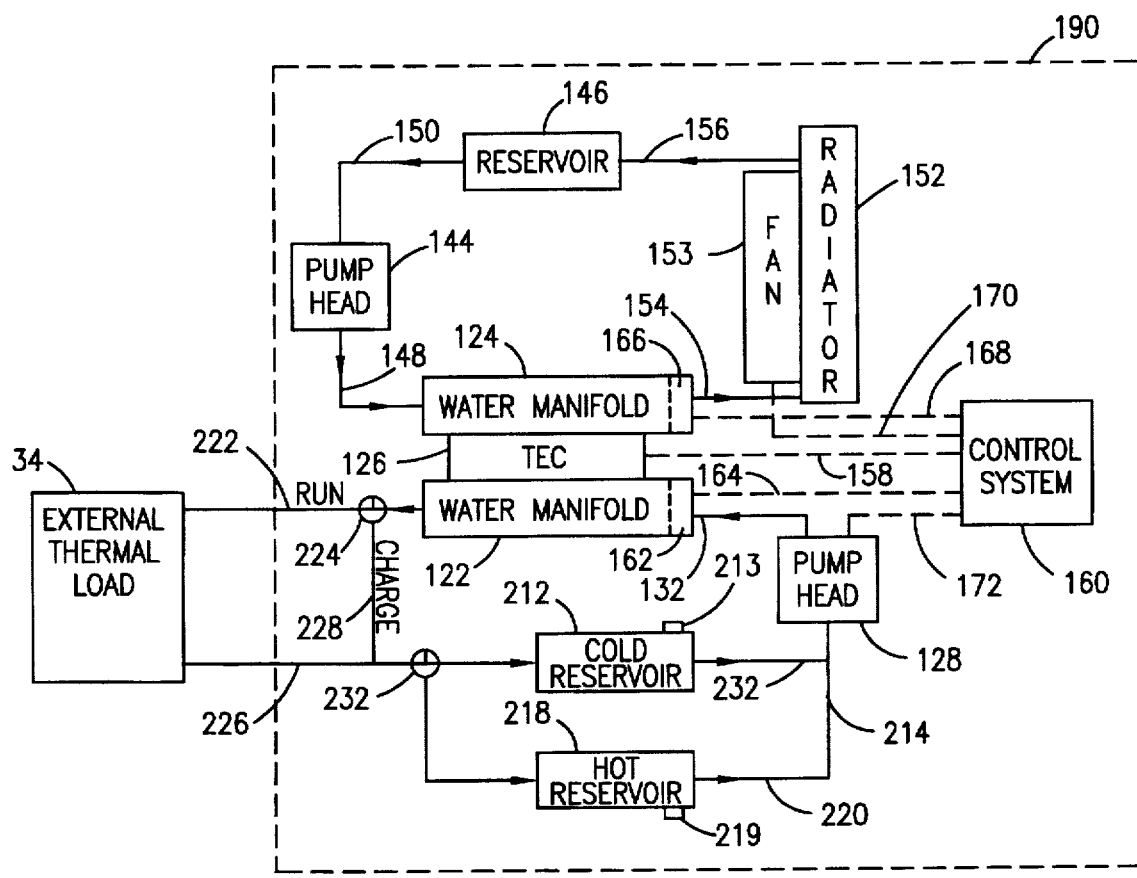
FIG. 11 is a schematic view showing an additional embodiment of the present invention which provides a quick changeover capability from the cooling mode to the heating mode or vice versa.

Referring now to FIG. 11, the reference numeral 210 indicates an additional embodiment of the present invention which provides a thermoelectric temperature control system with a quick changeover capability from the cooling mode to the heating mode or vice versa. Thermoelectric temperature control system 210, for either heating or cooling, includes a first liquid heat exchanger or water manifold 122 and a second liquid heat exchanger or water manifold 124. At least one thermoelectric device or module (TEC) 126 is positioned in contact with the first liquid heat exchanger 122 and the second liquid heat exchanger 124 for thermal conductivity therebetween. First pump head 128 is connected in fluid communication with first liquid heat exchanger 122 by conduit, pipe or hose 132, with first or cold reservoir 212 by conduits, pipes or hoses 214 and 216 and with second or hot reservoir 218 by conduits, pipes or hoses 214 and 220. It will be appreciated that first or cold reservoir 212 and second or hot reservoir 218 are large enough and have sufficient capacity to provide the function of a thermal capacitor during the charge time and during the intended use of the thermoelectric temperature control system 210 in supplying the active heating or cooling to the external thermal load 34.

First liquid heat exchanger 122 is also connected in fluid communication with external load 34 by conduit, pipe or hose 222. First valve 224, having a first position and a second position, is connected in conduit, pipe or hose 222. Cold reservoir 212 is also connected in fluid communication with external load 34 by conduit, pipe or hose 226. First valve 224 is connected to conduit, pipe or hose 226 by conduit, pipe or hose 228. Second valve 230, having a first position and a second position, is connected in conduit, pipe or hose 226. Hot reservoir 218 is also connected in fluid communication with external load 34 by conduit, pipe or hose 232, second valve 230 and conduit, pipe or hose 226.

Control system 160 provides power, of the correct polarity and duration, to thermoelectric device or module 126 via cable 158 so that the desired cooling or heating of the temperature control fluid 24 (such as water, glycol solution, etc.) flowing through first liquid heat exchanger 122 will be accomplished. Temperature sensor 162 is attached to first liquid heat exchanger 122 to provide a signal via cable 164 to the control system 160 indicative of the temperature of the first liquid heat exchanger 122. It will be appreciated that temperature control fluid 24 can be circulated through first liquid heat exchanger 122, first valve 224 positioned in the first position, external thermal load 34, second valve 230, either cold reservoir 212 or hot reservoir 218 (depending upon the position of second valve 230), first pump head 128 and back to first liquid heat exchanger 122. It will also be appreciated that temperature control fluid 24 can also be circulated through first liquid heat exchanger 122, first valve 224 positioned in the second position, second valve 230, either cold reservoir 212 or hot reservoir 218 (depending upon the position of second valve 230), first pump head 128 and back to first liquid heat exchanger 122 thereby bypassing the external thermal load 34 during the charge time of the thermoelectric temperature control system 210.

In applications where the charge time is to be significantly reduced, the present invention provides an external port 213 in cold reservoir 212 and an external port 219 in hot reservoir 218 which may be used to add materials which have already been phase changed by other means.

Second pump head 144 is connected in fluid communication with second liquid heat exchanger 124 and with third reservoir 146 by conduits, pipes or hoses 148 and 150, respectively. It will be appreciated that first pump head 128 and second pump head 144 are combined with a pump motor to comprise a two head pump. Second liquid heat exchanger 124 is also connected in fluid communication with radiator 152 via conduit, pipe or hose 154. Radiator 152 is also connected in fluid communication with reservoir 146 via conduit, pipe or hose 156. Fan 153 is positioned to blow or pass a gaseous fluid, such as air, etc., over radiator 152 to cool the liquid passing through radiator 152. Using radiator 152 to remove the heat or cold from the liquid passing through second liquid heat exchanger 124, the liquid can be repeatedly recirculated to improve the efficiency of the system. Typically, this liquid is circulated counter current to the flow of the temperature control fluid 24 but other embodiments providing co-flow or cross-flow are available embodiments. Temperature sensor 166 is attached to second liquid heat exchanger 124 to provide a signal via cable 168 to the control system 160 indicative of the temperature of the second liquid heat exchanger 124. Fan 153 is powered and controlled by control system 160 via cable 170. It will be appreciated that a liquid with a larger thermal capacity than air is circulated through second liquid heat exchanger 124, radiator 152, reservoir 146, second pump head 144 and back to second liquid heat exchanger 124.

Control system 160 receives an indication of the temperature of the temperature control fluid 24 from the temperature sensor 162 and of the temperature of the liquid flowing through the second liquid heat exchanger 124 from the temperature sensor 166. Based upon these sensed temperatures, control system 160 sends controlling signals to thermoelectric device or module 126, to pump motor (via cable 172) to control first pump head 128 and second pump head 144 and to fan 153 to maintain the temperature of the temperature control fluid 24 at the desired value for the particular function being performed.

With further reference to FIG. 11, in preparation for use of the thermoelectric temperature control system 210 where heating and cooling are both required at the external thermal load 34, power is applied to the thermoelectric temperature control system 210. First valve 224 is placed in the second position to connect conduit, pipe or hose 222 to conduit, pipe or hose 226 through conduit, pipe or hose 228 so as to bypass external thermal load 34. Second valve 230 is positioned, for example, in the first position to connect conduit, pipe or hose 226 to cold reservoir 212. The thermoelectric temperature control system 210 is run (as previously discussed) for a period of time called the charge time to cool the temperature control fluid 24 in cold reservoir 212. Upon completion of the charge time for the temperature control fluid 24 in cold reservoir 212, second valve 230 is positioned in the second position to connect conduit, pipe or hose 226 to conduit, pipe or hose 232 and hot reservoir 218. The polarity of the power to the thermoelectric device or module 126 is reversed and the thermoelectric temperature control system 210 is again run for a period of time to heat the temperature control fluid 24 in hot reservoir 218. Upon completion of the charge time for the temperature control fluid 24 in hot reservoir 218, the thermoelectric temperature control system 210 is ready to supply heating or cooling to the external thermal load 34 upon proper positioning of first valve 224 and second valve 230 and the providing of proper polarity of the power applied to the thermoelectric device or module 126.

From the foregoing detailed description, it can be appreciated that each of the embodiments of the present invention is capable of providing an improved thermoelectric temperature control system to provide additional heating or cooling capabilities not available by the active heating or cooling of the thermoelectric temperature control system without the present invention.

While particular embodiments of the present invention have been described, it will be appreciated by those skilled in the art that various modifications, alternatives, variations, etc., may be made without departing from the spirit and scope of the invention as defined in the appended claims.

What is claimed is:

1. An improved thermoelectric temperature control system for selectively heating or cooling a temperature control fluid to be provided through an exit conduit to an external thermal load and returned to the system through an inlet conduit, said system having at least a first liquid heat exchanger, a thermoelectric module in thermal conductivity with the liquid heat exchanger, a heat sink in thermal conductivity with the thermoelectric module, a pump and connecting conduits to move the temperature control fluid from the inlet conduit through the pump and liquid heat exchanger to the exit conduit, and power and control electronics to activate the pump and thermoelectric module, said improvement comprising:

a thermal capacitor connected for fluid communication with said external thermal load and said thermoelectric temperature control system to provide thermal wattage to said external thermal load via the temperature control fluid in addition to the thermal wattage provided to said external thermal load by said thermoelectric temperature control system via the temperature control fluid during the real-time use of said thermoelectric temperature control system; and wherein said thermal capacitor includes a thermal storage tank for storing temperature control fluid; and valve means connected in fluid communication to the thermal storage tank, the external thermal load and the thermoelectric temperature control system and structured to be positioned in either a first position or a second position to allow fluid flow of said temperature control fluid through said thermal storage tank, said valve means and said thermoelectric temperature control system when positioned in the first position and to allow fluid flow of said temperature control fluid through said thermal storage tank, said valve means, said external thermal load and said thermoelectric temperature control system when positioned in the second position.

2. The improvement as set forth in claim 1 further including pump means positioned to provide additional pumping force to said temperature control fluid.

3. The improvement as set forth in claim 21 wherein said thermal capacitor comprises:

a second liquid heat exchanger comprising a housing having a conduit for passing temperature control fluid therethrough;

thermal storage material filling the space between the housing and the conduit and in thermal communication with said conduit; and valve means connected in fluid communication to the conduit of the second liquid heat exchanger, the external thermal load and the thermoelectric temperature control system and structured to be positioned in either a first position or a second position to allow fluid flow of said temperature control fluid through said conduit, said valve means and said thermoelectric temperature control system when positioned in the first position and to allow fluid flow of said temperature control fluid through said conduit, said valve means, said external thermal load and said thermoelectric temperature control system when positioned in the second position.

4. The improvement as set forth in claim 4 further including pump means positioned to provide additional pumping force to said temperature control fluid.

5. The improvement as set forth in claim 3 wherein said thermal storage material comprises a phase change material.

6. The improvement as set forth in claim 5 wherein said phase change material comprises a wax.

7. The improvement as set forth in claim 5 wherein said phase change material comprises a paraffin.

8. The improvement as set forth in claim 5 wherein said phase change material comprises a salt.

9. The improvement as set forth in claim 3 further including pump means in series with a storage tank, said pump means and said storage tank connected in fluid communication with said thermal storage material to circulate said thermal storage material in and out of said storage tank.

10. An "add-on unit" apparatus to be connected between the exit conduit and the inlet conduit for temperature control fluid of a thermoelectric temperature control system for selectively heating or cooling the temperature control fluid to be provided to an external thermal load, said apparatus comprising:

a thermal capacitor connected for fluid communication with said external thermal load and said thermoelectric temperature control system to provide thermal wattage to said external thermal load via the temperature control fluid in addition to the thermal Wattage provided to said external thermal load by said thermoelectric temperature control system via the temperature control fluid during the real-time use of said thermoelectric temperature control system, and wherein said thermal capacitor includes a thermal storage tank for storing temperature control fluid; and valve means connected in fluid communication to the thermal storage tank, the external thermal load and the thermoelectric temperature control system and structured to be positioned in either a first position or a second position to allow fluid flow of said temperature control fluid through said thermal storage tank, said valve means and said thermoelectric temperature control system when positioned in the first position and to allow fluid flow of said temperature control fluid through said thermal storage tank, said valve means, said external thermal load and said thermoelectric temperature control system when positioned in the second position.

11. The apparatus as set forth in claim 10 further including pump means positioned to provide additional pumping force to said temperature control fluid.

12. The apparatus as set forth in claim 10 wherein said thermal capacitor comprises:

a second liquid heat exchanger comprising a housing having a conduit for passing temperature control fluid therethrough;

thermal storage material filling the space between the housing and the conduit and in thermal communication with said conduit; and valve means connected in fluid communication to the conduit of the second liquid heat exchanger, the external thermal load and the thermoelectric temperature control system and structured to be positioned in either a first position or a second position to allow fluid flow of said temperature control fluid through said conduit, said valve means and said thermoelectric temperature control system when positioned in the first position and to allow fluid flow of said temperature control fluid through said conduit, said valve means, said external thermal load and said thermoelectric temperature control system when positioned in the second position.

13. The apparatus as set forth in claim 12 further including pump means positioned to provide additional pumping force to said temperature control fluid.

14. The apparatus as set forth in claim 12 wherein said thermal storage material comprises a phase change material.

15. The apparatus as set forth in claim 14 wherein said phase change material comprises a wax.

16. The apparatus as set forth in claim 14 wherein said phase change material comprises a paraffin.

17. The apparatus as set forth in claim 14 wherein said phase change material comprises a salt.

18. The apparatus as set forth in claim 12 further including pump means in series with a storage tank, said pump means and said storage tank connected in fluid communication with said thermal storage material to circulate said thermal storage material in and out of said storage tank.

19. A thermoelectric temperature control system for selectively heating or cooling a temperature control fluid to be provided through a liquid outlet to an external thermal load and returned to the system through a liquid inlet, said thermoelectric temperature control system comprising:

a first liquid heat exchanger;

a second liquid heat exchanger;

a thermoelectric module in thermal conductivity with both the first and second liquid heat exchangers;

a pump having a first head and a second head;

a first reservoir;

first conduit means connecting said first liquid heat exchanger, said first head of the pump and said first reservoir in fluid communication with the external thermal load to create flow of the temperature control fluid therebetween;

a second reservoir;

a radiator;

second conduit means connecting said second liquid heat exchanger, said second head of the pump, said second reservoir and the radiator in fluid communication to create fluid flow therebetween;

a thermal capacitor connected for fluid communication with said external thermal load and said thermoelectric temperature control system to provide thermal wattage to said external thermal load via the temperature control fluid in addition to the thermal wattage provided to said external thermal load by said thermoelectric temperature control system via the temperature control fluid during the real-time use of said thermoelectric temperature control system; and includes:

a thermal storage tank for storing temperature control fluid; and valve means connected in fluid communication to the thermal storage tank, the external thermal load and the thermoelectric temperature control system and structured to be positioned in either a first position or a second position to allow fluid flow of said temperature control fluid through said thermal storage tank, said valve means and said thermoelectric temperature control system when positioned in the first position and to allow fluid flow of said temperature control fluid through said thermal storage tank, said valve means, said external thermal load and said thermoelectric temperature control system when positioned in the second position.

20. The system as set forth in claim 19 further including pump means positioned to provide additional pumping force to said temperature control fluid.

21. The system as set forth in claim 19 wherein said thermal capacitor comprises:

a second liquid heat exchanger comprising a housing having a conduit for passing temperature control fluid therethrough;

thermal storage material filling the space between the housing and the conduit and in thermal communication with said conduit; and valve means connected in fluid communication to the conduit of the second liquid heat exchanger, the external thermal load and the thermoelectric temperature control system and structured to be positioned in either a first position or a second position to allow fluid flow of said temperature control fluid through said conduit, said valve means and said thermoelectric temperature control system when positioned in the first position and to allow fluid flow of said temperature control fluid through said conduit, said valve means, said external thermal load and said thermoelectric temperature control system when positioned in the second position.

22. The system as set forth in claim 21 further including pump means positioned to provide additional pumping force to said temperature control fluid.

23. The system as set forth in claim 21 wherein said thermal storage material comprises a phase change material.

24. The system as set forth in claim 23 wherein said phase change material comprises a wax.

25. The system as set forth in claim 23 wherein said phase change material comprises a paraffin.

26. The system as set forth in claim 23 wherein said phase change material comprises a salt.

27. The system as set forth in claim 21 further including pump means in series with a storage tank, said pump means and said storage tank connected in fluid communication with said thermal storage material to circulate said thermal storage material in and out of said storage tank.

28. A thermoelectric temperature control system for selectively heating or cooling a temperature control fluid to be provided through a liquid outlet to an external thermal load and returned to the system through a liquid inlet, said thermoelectric temperature control system comprising:

a first liquid heat exchanger;

a second liquid heat exchanger:

a thermoelectric module in thermal conductivity with both the first and second liquid heat exchangers;

a pump a reservoir;

first conduit means connecting said first liquid heat exchanger, said pump and said reservoir in fluid communication with the external thermal load to create flow of the temperature control fluid therebetween;

an external source of water;

means to carry the water away from said thermoelectric temperature control system;

second conduit means connecting said second liquid heat exchanger, said external source of water and said means to carry the water away from said thermoelectric temperature control system in fluid communication to create fluid flow therebetween; and further comprising a thermal capacitor connected for fluid communication with said external thermal load and said thermoelectric temperature control system to provide thermal wattage to said external thermal load via the temperature control fluid in addition to the thermal wattage provided to said external thermal load by said thermoelectric temperature control system via the temperature control fluid during the real-time use of said thermoelectric temperature control system.

29. The system as set forth in claim 28 wherein said thermal capacitor comprises:

a thermal storage tank for storing temperature control fluid; and valve means connected in fluid communication to the thermal storage tank, the external thermal load and the thermoelectric temperature control system and structured to be positioned in either a first position or a second position to allow fluid flow of said temperature control fluid through said thermal storage tank, said valve means and said thermoelectric temperature control system when positioned in the first position and to allow fluid flow of said temperature control fluid through said thermal storage tank, said valve means, said external thermal load and said thermoelectric temperature control system when positioned in the second position.

30. The system as set forth in claim 29 further including pump means positioned to provide additional pumping force to said temperature control fluid.

31. The system as set forth in claim 28 wherein said thermal capacitor comprises:

a second liquid heat exchanger comprising a housing having a conduit for passing temperature control fluid therethrough;

thermal storage material filling the space between the housing and the conduit and in thermal communication with said conduit; and valve means connected in fluid communication to the conduit of the second liquid heat exchanger, the external thermal load and the thermoelectric temperature control system and structured to be positioned in either a first position or a second position to allow fluid flow of said temperature control fluid through said conduit, said valve means and said thermoelectric temperature control system when positioned in the first position and to allow fluid flow of said temperature control fluid through said conduit, said valve means, said external thermal load and said thermoelectric temperature control system when positioned in the second position.

32. The system as set forth in claim 31 further including pump means positioned to provide additional pumping force to said temperature control fluid.

33. The system as set forth in claim 31 wherein said thermal storage material comprises a phase change material.

34. The system as set forth in claim 33 wherein said phase change material comprises a wax.

35. The system as set forth in claim 33 wherein said phase change material comprises a paraffin.

36. The system as set forth in claim 33 wherein said phase change material comprises a salt.

37. The system as set forth in claim 31 further including pump means in series with a storage tank, said pump means and said storage tank connected in fluid communication with said thermal storage material to circulate said thermal storage material in and out of said storage tank.

38. A thermoelectric temperature control system for selectively heating or cooling a temperature control fluid to be provided through a liquid outlet to an external thermal load and returned to the system through a liquid inlet, said thermoelectric temperature control system comprising:

a first liquid heat exchanger;

a second liquid heat exchanger;

a thermoelectric module in thermal conductivity with both the first and second liquid heat exchangers;

a pump having a first head and a second head;

a first reservoir;

a second reservoir;

a first valve structured to be positioned in either a first position or a second position;

a second valve structured to be positioned in either a first position or a second position;

first conduit means connecting said first valve, said first liquid heat exchanger, said first head of the pump, said first reservoir and said second valve in fluid communication with the external thermal load to create flow of the temperature control fluid therebetween when said first valve is in said first position and said second valve is in said first position;

second conduit means connecting said first valve, said first liquid heat exchanger, said first head of the pump, said second reservoir and said second valve in fluid communication with the external thermal load to create flow of the temperature control fluid therebetween when said first valve is in said first position and said second valve is in said second position;

third conduit means connecting said first valve, said first liquid heat exchanger, said first head of the pump, said first reservoir and said second valve in fluid communication to create flow of the temperature control fluid therebetween when said first valve is in said second position and said second valve is in said first position;

fourth conduit means connecting said first valve, said first liquid heat exchanger, said first head of the pump, said second reservoir and said second valve in fluid communication to create flow of the temperature control fluid therebetween when said first valve is in said second position and said second valve is in said second position;

a third reservoir;

a radiator; and fifth conduit means connecting said second liquid heat exchanger, said second head of the pump, said third reservoir and the radiator in fluid communication to create fluid flow there between.

39. The system as set forth in claim 38 further comprising blower means positioned to pass gaseous fluid over said radiator.

* * * * *

UNITED STATES PATENT AND TRADEMARK OFFICE
CERTIFICATE OF CORRECTION

PATENT NO. : 5,711,155
DATED : Jan. 27, 1998
INVENTOR(S) : DeVilbiss et al.

It is certified that error appears in the above-identified patent and that said Letters Patent is hereby corrected as shown below:

Column 8, line 60          After "Fan"
                           Insert --153 is powered and
                           controlled by control system 160
                           via--

Column 10, line 51         Replace "9"
                           With --190--

Column 13, line 34         Replace "21"
                           With --1--

Column 15, line 40         Before "includes:"
                           Insert --wherein said thermal
                           capacitor--

Column 16, line 35         Replace ":"
                           With --;--

Signed and Sealed this

Twenty-seventh Day of October, 1998

Attest:

BRUCE LEHMAN

*Attesting Officer*            *Commissioner of Patents and Trademarks*